United States Patent
Chow

(10) Patent No.: US 7,264,702 B1
(45) Date of Patent: Sep. 4, 2007

(54) TOTAL ANALYTE QUANTITATION

(75) Inventor: Calvin Y. H. Chow, Portola Valley, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 558 days.

(21) Appl. No.: 10/702,115

(22) Filed: Nov. 5, 2003

Related U.S. Application Data

(63) Continuation of application No. 09/835,085, filed on Apr. 12, 2001, now Pat. No. 6,733,645.

(60) Provisional application No. 60/198,511, filed on Apr. 18, 2000, provisional application No. 60/224,975, filed on Aug. 16, 2000.

(51) Int. Cl.
*G01N 27/447* (2006.01)

(52) U.S. Cl. ............................. 204/452; 204/453

(58) Field of Classification Search .............. 204/450, 204/451, 453, 600, 601, 602, 604, 452; 422/70, 422/100, 99, 68.1
See application file for complete search history.

(56) References Cited

U.S. PATENT DOCUMENTS

| | | |
|---|---|---|
| 3,706,877 A | 12/1972 | Clifford et al. |
| 4,390,403 A | 6/1983 | Batchelder |
| 4,666,578 A | 5/1987 | Yamamoto |
| 4,908,112 A | 3/1990 | Pace |
| 5,126,022 A | 6/1992 | Soane et al. |
| 5,498,392 A | 3/1996 | Wilding et al. |
| 5,571,410 A | 11/1996 | Swedberg et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,603,351 A | 2/1997 | Cherukuri et al. |
| 5,635,358 A | 6/1997 | Wilding et al. |
| 5,637,469 A | 6/1997 | Wilding et al. |
| 5,699,157 A | 12/1997 | Parce |
| 5,750,015 A | 5/1998 | Soane et al. |
| 5,779,868 A | 7/1998 | Parce et al. |
| 5,800,690 A | 9/1998 | Chow et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |

(Continued)

FOREIGN PATENT DOCUMENTS

EP  620432  10/1994

(Continued)

OTHER PUBLICATIONS

Cohen, C.B. et al. "A Microchip-Based Enzyme Assay for Protein Kinase A" *Anal. Chem.* (1999) 273:89-97.

(Continued)

*Primary Examiner*—Alex Noguerola
(74) *Attorney, Agent, or Firm*—Ann C. Peterson; Donald R. McKenna

(57) ABSTRACT

Methods for determining total analyte concentrations and amounts, especially in combination with analyte separations are provided. Microfluidic devices are used to separate analyte mixtures and detect the individual analytes. Signal areas are summed for each individual analyte to quantitate the total analyte amount. Separate measurements of the total analyte sample are also used to determine total analyte concentration.

6 Claims, 3 Drawing Sheets

U.S. PATENT DOCUMENTS

| | | | |
|---|---|---|---|
| 5,880,071 | A | 3/1999 | Parce et al. |
| 5,882,465 | A | 3/1999 | McReynolds |
| 5,885,470 | A | 3/1999 | Parce et al. |
| 5,942,443 | A | 8/1999 | Parce et al. |
| 5,948,227 | A | 9/1999 | Dubrow |
| 5,955,028 | A | 9/1999 | Chow |
| 5,957,579 | A | 9/1999 | Kopf-Sill et al. |
| 5,958,203 | A | 9/1999 | Parce et al. |
| 5,958,694 | A | 9/1999 | Nikiforov |
| 5,959,291 | A | 9/1999 | Jensen |
| 5,964,995 | A | 10/1999 | Nikiforov et al. |
| 5,965,001 | A | 10/1999 | Chow et al. |
| 5,965,410 | A | 10/1999 | Chow et al. |
| 5,972,187 | A | 10/1999 | Parce et al. |
| 5,976,336 | A | 11/1999 | Dubrow et al. |
| 5,989,402 | A | 11/1999 | Chow et al. |
| 6,001,231 | A | 12/1999 | Kopf-Sill |
| 6,004,515 | A | 12/1999 | Parce et al. |
| 6,011,252 | A | 1/2000 | Jensen |
| 6,012,902 | A | 1/2000 | Parce |
| 6,042,710 | A | 3/2000 | Dubrow |
| 6,046,056 | A | 4/2000 | Parce et al. |
| 6,068,752 | A | 5/2000 | Dubrow et al. |
| 6,071,478 | A | 6/2000 | Chow |
| 6,074,725 | A | 6/2000 | Kennedy |
| 6,080,295 | A | 6/2000 | Parce et al. |
| 6,375,817 | B1 | 4/2002 | Taylor et al. |
| 6,733,645 | B1 * | 5/2004 | Chow .................. 204/453 |
| 2002/0008029 | A1 * | 1/2002 | Williams et al. ........... 204/453 |

FOREIGN PATENT DOCUMENTS

| | | |
|---|---|---|
| WO | WO-9604547 | 2/1996 |
| WO | WO-9702357 | 1/1997 |
| WO | WO-9800231 | 1/1998 |
| WO | WO-9800705 | 1/1998 |
| WO | WO-9800707 | 1/1998 |
| WO | WO-9802728 | 1/1998 |
| WO | WO-9805424 | 2/1998 |
| WO | WO-9822811 | 5/1998 |
| WO | WO-9845481 | 10/1998 |
| WO | WO-9845929 | 10/1998 |
| WO | WO-9846438 | 10/1998 |
| WO | WO-9849548 | 11/1998 |
| WO | WO-9855852 | 12/1998 |
| WO | WO-9856956 | 12/1998 |
| WO | WO-9900649 | 1/1999 |
| WO | WO-9910735 | 3/1999 |
| WO | WO-9912016 | 3/1999 |
| WO | WO-9916162 | 4/1999 |
| WO | WO-9919056 | 4/1999 |
| WO | WO-9919516 | 4/1999 |
| WO | WO-9929497 | 6/1999 |
| WO | WO-9956954 | 11/1999 |
| WO | WO-9964848 | 12/1999 |
| WO | WO-0009753 | 2/2000 |
| WO | WO-0114064 | 3/2001 |
| WO | WO-0131322 | 5/2001 |

OTHER PUBLICATIONS

Dasgupta, P.K. et al., "Electroosmosis: A Reliable Fluid Propulsion System for Flow Injection Analysis," *Anal. Chem.* (1994) 66:1792-1798.

Jacobson, S.C. et al., "Fused Quartz Substrates for Microchip Electrophoresis," *Anal. Chem.* (1995) 67: 2059-2063.

Manz, A. et al., "Electroosmotic Pumping and Electrophoretic Separations for Miniaturized Chemical Analysis Systems," *J. Micromach. Microeng.* (1994) 4: 257-265.

Ramsey, J.M. et al., "Microfabricated Chemical Measurement Systems," *Nature Medicine* (1995) 1:1093-1096.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow within a Manifold of Capillaries on a Glass Chip," *Anal. Chem.* (1994) 66:3485-3491.

Sundberg, S.A. "High-throughput and ultra-high-throughput screening: solution and cell-based approaches" Current Opin. In Biotechnology (2000) 11:47-53.

Verheggen, P.E.M. et al. "Simple Sampling Device for Capillary Isotachophoresis and Capillary Zone Electrophoresis" *J. Chromatog.* (1988) 452:615-622.

* cited by examiner

US 7,264,702 B1

TOTAL ANALYTE QUANTITATION

CROSS-REFERENCES TO RELATED APPLICATIONS

This application is a continuation of U.S. patent application Ser. No. 09/835,085 filed Apr. 12, 2001 now U.S. Pat. No. 6,733,645. Pursuant to 35 U.S.C. §§ 119 and/or 120, and any other applicable statute or rule, this application also claims the benefit of and priority to both U.S. Ser. No. 60/198,511, filed on Apr. 18, 2000 and U.S. Ser. No. 60/224,975, filed on Aug. 16, 2000, the disclosures of which are incorporated herein by reference.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Biological molecules, such as proteins and nucleic acids are routinely fractionated and characterized, e.g., by capillary electrophoresis or using microfluidic separation technology. For example, U.S. Pat. No. 5,948,227 by Dubrow, entitled "Methods and Systems for Performing Electrophoretic Molecular Separations," describes methods for electrophoretically separating molecular and macromolecular species in microfluidic devices.

Electrophoretic forces are typically used to separate materials in microfluidic devices, e.g., relying upon the electrophoretic mobility of charged species within an electric field applied to the material. Electrophoretic movement is used to separate mixtures of components as they move through a microfluidic channel. Signal peak area of separated components is typically used to assess the extent of reactions, reaction rate constants, concentration of reactants, products, separated components, and a variety of other chemical and biochemical parameters.

Just as in traditional capillary electrophoresis, electrokinetic sample introduction in a microfluidic device biases sample introduction. The electric fields can cause preferential movement of reagents due to differences in their mass to charge ratio, e.g., highly charged materials move to the front or back of a fluid plug. This effect is desirable when attempting to electrokinetically separate various compounds, but inhibits the ability to obtain measurements relating to entire samples, e.g., unseparated unbiased samples. For example, it is often desirable to identify the total concentration, e.g., of nucleic acids or proteins, in a sample in addition to the concentration of each nucleic acid fragment, e.g., after separation.

The calculation of kinetic constants in flowing systems has also been described. For example, published PCT application WO 98/56956, by Kopf-Sill et al., entitled "Apparatus and Methods for Correcting Variable Velocity in Microfluidic Systems," describes methods of determining concentration, e.g., after an electrokinetically biased sample introduction, using variable velocities, e.g., of reactants and products. This reference also describes, e.g., the use of gated injections to achieve representative sample aliquots and other related phenomena.

The present invention provides methods and apparatus for obtaining representative or unbiased sample aliquots that are used to determine, e.g., total analyte concentrations. The methods and apparatus of the present invention provide these features and many others that will be apparent upon complete review of the following disclosure.

SUMMARY OF THE INVENTION

The present application provides methods for separating two or more analytes, e.g., in a microchannel, and determining a total analyte concentration for the two or more analytes. For example, a sample, e.g., a mixture of nucleic acid fragments, is optionally separated, the concentration or amount of each individual analyte in the sample determined, and the concentration of all analytes together determined. The methods typically involve summation of individual analyte concentrations using a representative sample aliquot, or alternatively, measurement of the total analyte concentration prior to separation.

In one aspect, a method for separating analytes and determining a total analyte concentration or amount is provided. The method comprises flowing at least two analytes through a first channel, e.g., electrokinetically or under pressure. The analytes typically flow into an intersection of the first channel with a separation channel. After a specified time, the analytes at the intersection are injected into the separation channel. The analytes are then separated, e.g., electrophoretically, resulting in two or more separated analytes. The analytes are then detected, resulting in, e.g., two or more signals. The two or more signals are used to determine the total analyte concentration, e.g., by summation of the two or more signals, e.g., summation of the signal peak areas or peak heights corresponding to individual analyte concentrations. The concentration or amount of each individual analyte is also optionally determined, e.g., to produce a ratio of the amount of at least one of the analytes to the total analyte amount or to a portion of the total analyte amount.

Typically, the analytes have different electrokinetic mobilities, wherein at least one of the analytes comprises a slowest analyte. Waiting the specified time to inject the analytes into the separation channel typically involves waiting until the slowest analyte reaches the intersection. By waiting until the slowest analyte has reached the intersection, a representative sample aliquot is obtained such that a total analyte concentration for the sample is optionally determined, e.g., after separation of the injected sample.

In another aspect, the method of separating two or more analytes and determining a total analyte concentration or amount comprises flowing, e.g., electrokinetically or under pressure, at least two analytes through a first channel region and through a measurement channel region. The analytes are detected, e.g., unseparated, in the measurement channel region, thereby determining the total analyte concentration or amount. Detection in the measurement channel typically leads to a signal that increases in value until it reaches a constant value, which constant value represents the total analyte concentration, e.g., after both slow and fast flowing analytes have reached a detection region. The analytes are then optionally injected into a separation channel, separated, e.g., electrophoretically, and detected. Concentrations or amounts of each individual analyte are optionally determined based on signals detected after separation of the analytes. Ratios of the amount of one or more of the separated analytes to the total analyte amount or to a portion of the total analyte amount are also optionally determined.

In another aspect, the invention provides systems for separating two or more analytes and determining a total analyte concentration or amount. Such a system typically comprises a microfluidic device comprising a body structure having a plurality of microscale channels disposed therein. The microscale channels typically comprise a first channel region for flowing one or more analytes, and a measurement channel region fluidly coupled to the first channel region. The measurement channel is used to obtain a total analyte concentration, e.g., after all analytes have had time to reach a detection channel region. Typically the devices include a separation channel fluidly coupled to the first channel region and two detection regions. A first detection region is typically positioned proximal to the measurement channel region and a second detection region is typically positioned proximal to the separation channel. The first detection region is typically used to detect the total analyte concentration or amount and the second detection region is typically used to detect individual analytes, e.g., after separation.

The system further comprises a fluid direction system fluidly coupled to the microfluidic device. The fluid direction system directs movement of the analytes through the first channel region; movement of the analytes from the first channel region into the measurement channel region; movement of the analytes through the first detection region; movement of the analytes from the first channel into the separation channel; and, movement of the separated analytes through the second detection region. The fluid direction system typically comprises one or more fluid control elements, such as pressure sources or electrokinetic controllers, fluidly coupled or air-coupled to the plurality of microscale channels.

A detection system is also included in the systems of the invention to detect total analyte sample aliquots and separated analytes. A detection system is typically positioned proximal to one or more of the first detection region or the second detection region. The detection system detects the analytes in the first detection region, resulting in a total analyte signal corresponding to the total analyte concentration or amount. The detection system also detects the separated analytes in the second detection region, resulting in two or more analyte signals, which two or more analyte signals correspond to the two or more separated analytes. The detection system optionally comprises a single detector positioned proximal to the first detection region and the second detection region or a first detector positioned proximal to the first detection region and a second detector positioned proximal to the second detection region.

Systems of the invention also optionally comprise a computer operably coupled to the detection system. The computer receives the total analyte signal and the two or more analyte signals. The computer typically comprises software comprising at least a first instruction set and a second instruction set. The instruction sets typically determine the total analyte concentration or amount from the total analyte signal and the concentration or amount of each individual analyte from the two or more analyte signals. Additional instruction sets are optionally provided to sum the individual analyte signals, thus determining the total analyte concentration or amount and/or determine a ratio of the amount of one or more analyte to the total analyte amount or to a portion of the total analyte amount.

DETAILED DISCUSSION OF THE INVENTION

Figure 1:
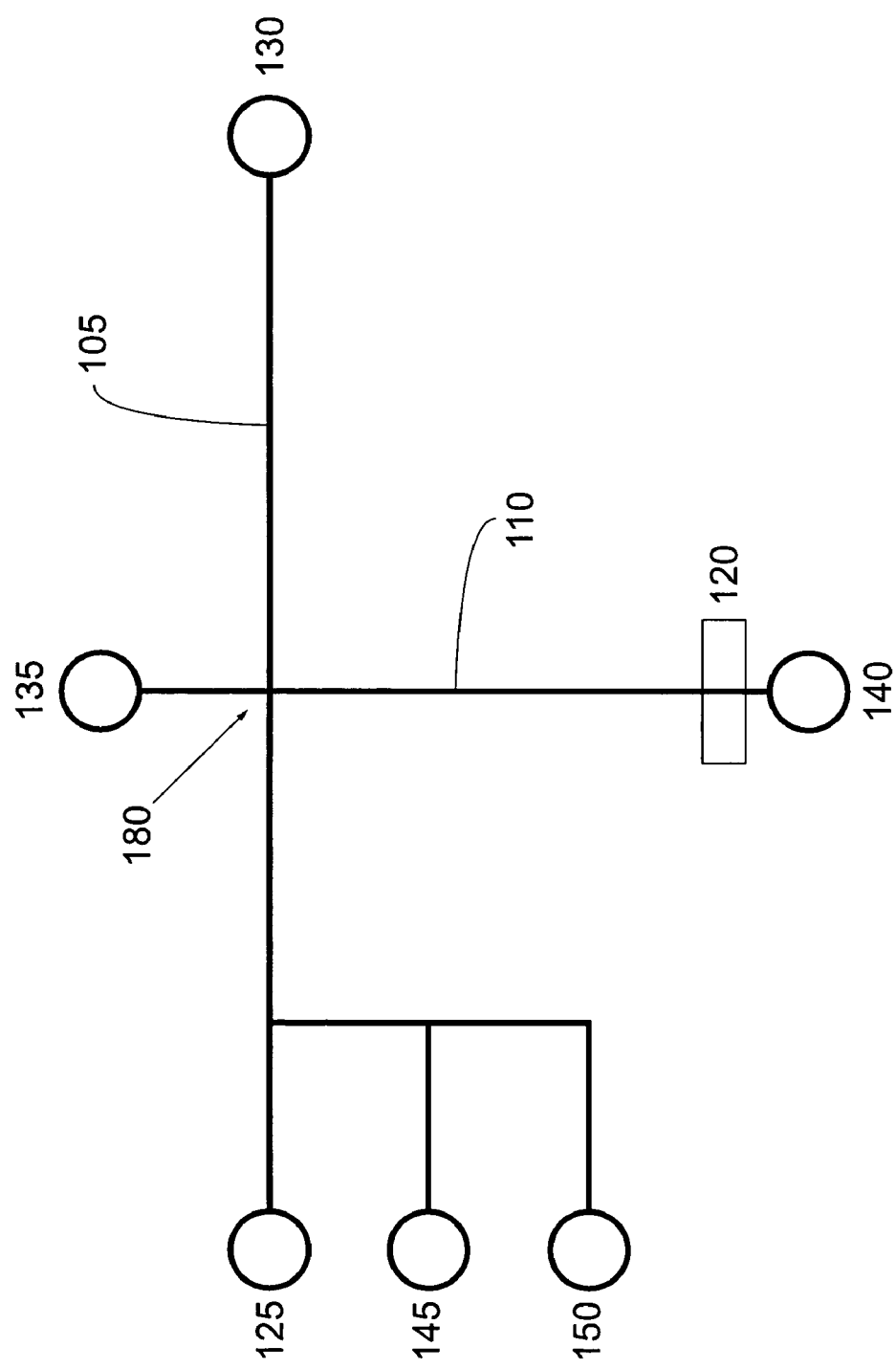
FIG. 1: Schematic illustration of a microfluidic channel configuration optionally used to determine total analyte concentration.

The present invention provides methods of providing total analyte quantitation on a sample. For example, a sample comprising a mixture of analytes, e.g., proteins or nucleic acids, has a total analyte concentration and an individual analyte concentration for each analyte in the mixture. In one embodiment, the present invention provides a representative aliquot of the sample. The representative aliquot is separated and the individual signal peak areas are summed to provide the total analyte concentration. In a second embodiment, a sample is flowed through a measurement channel region and detected in an unseparated format.

When a representative sample aliquot is separated, the individual analyte signal peak areas are optionally summed and normalized, e.g., for migration time, to provide the total analyte concentration. A representative sample aliquot is obtained, e.g., in a microfluidic device under electrokinetic flow control, by waiting a specified time for both slow and fast moving analytes to move into the separation region. The present invention provides, e.g., methods for performing an electrokinetic separation on a representative aliquot to obtain a total analyte concentration or amount.

Prior to separation, total analyte concentration is optionally performed by detecting a sample until a constant value is achieved. For example, a sample is flowed through a microfluidic channel, e.g., electrokinetically such that fast and slow analytes move at different velocities. The signal value typically increases as the amount of analytes reaching the detector increases. Once a steady signal is observed, it provides an indication that a representative sample is being detected, e.g., both slow and fast moving analytes have reached the detector. Once a constant signal value is observed, the total analyte concentration is typically determined from the steady state signal.

In the present invention, a "mixture of analytes" refers to a combination, known or unknown, of biological components or analytes, e.g., proteins, enzymes, polypeptides, carbohydrates, nucleic acids, polynucleotides, or the like. The analytes can be in a complex mixture, such as blood, serum, cell extracts, or in a purified solution, such as a buffered solution of polypeptides or polynucleotides. Typical analytes include, but are not limited to, ribosomal RNA or messenger RNA, for which a ratio as well as a summation is used to determine concentration. Typically, the components are separated in channels of a microfluidic device.

Concentrations or amounts of the individual separated analytes are optionally determined after detection, e.g., based on signal area or height. The present invention provides methods of determining the total amount or concentration of analyte, e.g., the entire amount of nucleic acid in a sample, e.g., a blood or serum sample. The "total analyte concentration or amount" refers to the entire quantity or concentration of analytes or other components in a sample or the sum of the quantities of all of the individual components or analytes. For example, a sample comprising various nucleic acids, nucleic acid fragments, and the like has a total nucleic acid concentration or amount and a concentration or amount for each nucleic acid. Amounts, e.g., absolute amounts, are obtained by measuring the entire quantity present in the tested or metered sample aliquot and concentrations are measured by determining the amount of analyte present in a particular volume of sample, e.g., the volume of sample that is flowed past the detector.

A general description of analyte separation techniques relevant to the present invention, e.g., in microfluidic devices, is provided below. The determination of total analyte quantitation methods is then provided, e.g., using a representative separated sample or an unseparated sample, e.g., in a measurement channel. Systems and devices for performing analyte separations and total analyte quantitations, e.g., in combination are also described. Additional features will be apparent upon complete review.

I. Separation of Analytes

The samples, e.g., mixtures of analytes, in the present invention are typically separated in a separation region or separation channel of a microfluidic device. A sample, e.g., to be assayed, tested, or separated, is introduced into a first channel of the device, e.g., an introduction channel, under pressure or electrokinetic control. When pressure driven flow, e.g., from a vacuum source or electroosmotic pump, is used, the sample that is introduced typically has no electrokinetic bias associated with it. No charge is applied and therefore the molecules or analytes do not move or separate based on charge. Movement of the analytes is due to the application of pressure, as opposed to the application of charge. Therefore, two analytes, e.g., unhindered analytes not in a sizing gel matrix, with different charges and masses move in the same direction at substantially the same velocity. However, when electrokinetic driven flow is used to introduce analytes into, or flow analytes through, a channel, the analytes move through the channel with an electrokinetic bias, i.e., depending on mass to charge ratio. Therefore, some analytes will reach the end of the channel or a particular intersection before others.

From the first channel or introduction channel, a sample aliquot is injected, e.g., by cross-injection, into a separation channel. The cross-injection injects the sample aliquot at the intersection of the first channel and the separation channel into the separation channel. Electrokinetic forces typically control fluid flow in separation channels, e.g., to obtain electrophoretic separation of components or analytes based on mass/charge ratio or size difference. Typically, electrophoretic separation is used to separate the analytes in the mixture, e.g., to separate nucleic acid fragments of various lengths. Electrophoretic separation is the separation of substances achieved by applying an electric field to samples in a solution or gel. In its simplest form, it depends on the different velocities with which the substances or components move in the field. The velocities depend, e.g., on the charge and size of the substances, as well as the solution or gel used in the channel.

The separation channels or regions typically comprise a separation matrix. When the sample is flowed through the separation matrix, the components are separated, e.g., based on physical or chemical properties, such as molecular weight and/or charge. The separation matrix comprises, e.g., a polymer, a gel, a polymer solution, particles, coated surfaces, or the like.

Preferably, the channel, such as separation channel 110 in FIG. 1, is a polyacrylamide gel filled channel, or a polydimethylacrylamide/co-acrylic acid polymer filled channel on which the mixture of analytes is electrophoretically separated based on mass to charge ratio or molecular weight, when all molecules are similarly charged. Polyacrylamide used as a separation matrix in a microfluidic channel is optionally cross-linked or non-cross-linked. Preferably it is linear polyacrylamide, i.e., polydimethylacrylamide or polydimethylacrylamide/co-acrylic acid. Other possible polymers utilized include cellulose, agarose, and the like. If the components are detected as they exit the separation region, the components are optionally identified by their retention times.

Other gel electrophoretic media that are optionally placed in a separation channel or region of the invention include silica gels such as Davisil Silica, E. Merck Silica Gel, Sigma-Aldrich Silica Gel (all available from Supelco) in addition to a wide range of silica gels available for various purposes as described in the Aldrich catalogue/handbook (Aldrich Chemical Company, Milwaukee, Wis.). Preferred gel materials include agarose based gels, various forms of acrylamide based gels (reagents available from, e.g., Supelco, SIGMA, Aldrich, Sigma-Aldrich and many other sources), colloidal solutions, such as protein colloids (gelatins) and hydrated starches. For a review of electrophoretic separation techniques and polyacrylamide gels, see, e.g., The Encyclopedia of Molecular Biology, Kendrew (ed.) (1994); and, Gel Electrophoresis of Proteins: A Practical Approach, $2^{nd}$ edition Hames and Rickwood (Eds.) IRL Press, Oxford England, (1990).

Other types of separation matrices are also optionally used and discussed in U.S. patent application Ser. No. 09/093,832 filed Jun. 8, 1998, entitled "Microfluidic Matrix Localizations Apparatus and Methods," by Burd Mehta and Kopf-Sill. Alternate separation matrix media include low pressure chromatography media, such as non-ionic macroreticular and macroporous resins which adsorb and release components based upon hydrophilic or hydrophobic interactions, e.g., Amberchrom and Amberlite resins (available from Supelco), Dowex, and Duolite (all available from Supelco). Other optional media include affinity media for purification and separation, such as acrylic beads, agarose beads, cellulose, sepharose, or the like. In addition, a wide variety of resins and chromatography media are also available, e.g., from Supelco, Sigma, Aldrich, or the like, for example, biotin resins, dye resins, aluminas, carbopacks, and the like. For a review of chromatography techniques and media, see, e.g., Affinity Chromatography—A Practical Approach, Dean et al., (Eds.) IRL Press, Oxford (1985); and, Chromatographic Methods, $5^{th}$ Edition, Braithwaite et al., (1996).

For example, a processed protein sample, e.g., that has been desalted and denatured in SDS, is optionally electrophoresed in a linear polyacrylamide gel filled separation channel containing SDS to separate the proteins on the basis of molecular weight of the protein subunits. A detector is optionally positioned so that it detects the proteins that are stained in the gel with a fluorescent protein stain. The retention time of the proteins as they are electrophoresed through the gel is used with markers to measure the molecular weight of the proteins. The area under the curve or peak height for each protein is used to determine the concentration and/or amount of that protein. The present invention provides methods for determining the concentration of all proteins combined in addition to the individual protein concentrations.

Separation of the analytes produces a plurality of signals upon detection. Each signal corresponds to an individual analyte and is typically used to determine the concentration or amount of each analyte present in the sample (e.g., using the signal peak areas), and/or to identify the analyte (e.g., using the retention times). The total amount of analyte is optionally obtained by summing or adding the normalized, e.g., peak areas vs. migration velocity peak areas or heights of the various analyte signals. However, to obtain an accurate total analyte quantitation, a representative sample aliquot, e.g., containing both slow and fast moving analytes, is typically used, e.g., injected into the separation channel from the first channel. If a non-representative aliquot is injected, the total analyte concentration will be biased, e.g., for fast moving analytes that reach the intersection of the first channel and the separation channel before the slow moving analytes (and therefore are preferentially injected into the separation channel). The present invention provides methods for accurate total analyte quantitation as described below.

II. Determination of Total Analyte Concentration

Analytes are moved through channels, e.g., in microfluidic devices, by the application of pressure to the analytes, the application of an electrokinetic gradient, or combinations thereof. The application of the electrokinetic gradient to flow analytes through a channel introduces an electrokinetic bias to the analytes, resulting in slower and faster moving analytes. The present invention provides methods of obtaining representative sample aliquots, e.g., that overcome electrokinetic bias, that are subsequently used to determine total analyte concentration. Electrokinetic bias is overcome by waiting an appropriate time so that the detected sample aliquot contains representative amounts of each individual analyte, both slow and fast moving analytes. The waiting time is used because an initial sample aliquot, e.g., the first sample aliquot or portion to reach the detection region, contains faster moving analytes and very few of the slowest moving analytes. A sample aliquot detected or injected after the time required for the slowest analyte to reach the detection region or cross-injection region contains the slowest and fastest moving analytes from a continuously flowing sample, thereby providing a representative sample aliquot. For example, when a sample is introduced into an introduction channel with electrokinetic bias, a cross-injection is typically timed to insure that the slowest analyte is included in the injected volume, thereby obtaining a representative sample. Alternatively, unseparated analytes are detected as they flow through a detection region. Initially, the signal peak area increases as more and more analytes reach the detection region. Eventually the slower analytes reach the detection region and fast analytes are still being flowed through so the signal peak value becomes constant. A constant or steady state signal value indicates that a representative sample comprising slower and faster moving analytes is flowing past the detector. When pressure based flow is used, the analytes typically do not move with electrokinetic bias. Therefore all analytes may reach the detection region simultaneously providing a constant signal value representing the total analyte concentration.

A sample, e.g., a mixture of analytes, is typically injected into a microfluidic device through a first channel such as an introduction channel, a mixing channel, a cross-channel, or the like. Various reagents are optionally mixed with the sample, e.g., to perform an assay which generates a mixture of products to be separated. Typically electrokinetic, e.g., electrophoretic or electroosmotic, forces are used to flow the analytes through the channels of the invention. A portion of the sample, e.g., a sample aliquot, is then cross-injected into a separation channel, e.g., the volume of material at the intersection of the first channel with a separation channel is injected or flowed into the separation channel. The mixture of analytes is then typically electrophoretically separated.

For example, in FIG. 1 a sample is optionally flowed from reservoir 125, 145, 150, or the like into a first channel, e.g., channel 105. In some embodiments, the sample is flowed continuously for a period of time, e.g., until depleted, through the channels of the invention. When the sample flows across the intersection of channel 105 and separation channel 110, a sample aliquot or the portion of sample in the intersection is cross-injected into separation channel 110, e.g., by applying a voltage gradient between reservoir 135 and reservoir 140.

Figure 2:
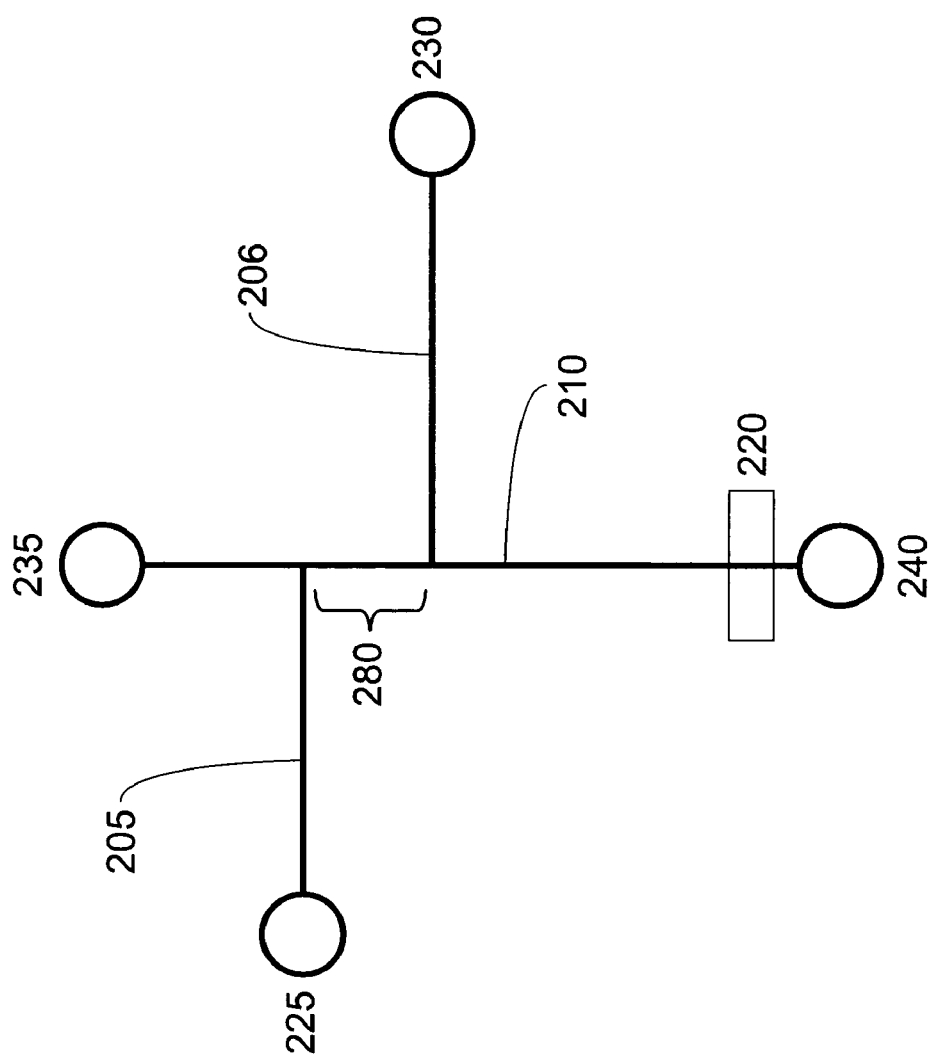
FIG. 2: Schematic illustration of a microfluidic channel configuration comprising an alternative intersection or junction for use in determining total analyte concentration.

In other embodiments, the intersection comprises a split intersection such that a larger volume of sample is injected into the separation channel. For example, see FIG. 2. In FIG. 2, a sample is flowed through a first channel that is divided into two portions, e.g., channel region 205 and channel region 206. The sample is flowed through channel region 205, through intersection region 280, and then into channel region 206. A cross injection into separation channel 210, e.g., achieved by a voltage gradient between reservoirs 235 and 240, injects the material within intersection region 280 into separation channel 210. A larger volume of fluid, e.g., the sample aliquot, is thereby injected into separation channel 210 from intersection region 280 than is injected into separation channel 110 from intersection 180 (as illustrated in FIG. 1).

The samples are typically flowed, e.g., continuously, for a period of time from the sample reservoirs, e.g., from reservoir 225 in FIG. 2, into the channels, e.g., channel 205. Therefore, when electrokinetic forces are applied to the channels, the samples and/or analytes move with an electrokinetic bias, e.g., analytes with varying mass to charge ratios move at different velocities through the channels. The faster moving analytes approach the intersection before the slower moving analytes, but after a period of time, the slower moving analytes also approach the intersection. Since the sample is continuously flowed, the faster analytes and the slower analytes will both be present at the intersection after a specified waiting time, e.g., the time for the slower analytes to reach the intersection. The specified time is at least as long as the time for the slowest analyte to reach the intersection of the first channel and the separation channel and possibly longer.

The specified time is optionally determined using markers, e.g., fluorescent markers that flow faster and/or slower than all analytes present in the sample. The markers are optionally detected to determine if all analytes of interest were included in the sample aliquot injected into the separation channel. If both slow and fast moving markers are detected, the data is then optionally used to provide a total analyte concentration measurement. In other embodiments, the time for the slowest analyte is optionally measured in an initial experiment using the same sample and then that time is selected as the specified time. In other embodiments, the analytes are known analytes for which flow rates at specified voltages are known or can be determined prior to total analyte quantitation. The specified waiting time is determined from the flow rate of the slowest moving analyte.

The method typically comprises detecting the signals from the separated analytes, which provide an indication of analyte concentrations, thereby optionally determining the concentration of each individual analyte. The concentration or amount is based upon the area under the curve of the peak detected for each analyte. The peak area is typically determined by integration of the area under the curve, e.g., using a digital electronic integrator. Alternative methods of determining peak area include, but are not limited to, cutting out, e.g., with scissors, the area concerned and weighing it, using a bar graph to approximate the area under the curve, and by counting squares, e.g., on graph paper on which the signal has been plotted. The areas of the peaks are correlated to the concentrations or amounts of analytes using standards, either internal or external, of known concentration or amount by methods well known to those of skill in the art. If the amount is desired, the amount of fluid passing the detector is also measured. Peak heights are also optionally used to determine concentration if separation conditions, e.g., temperature, flow rate, and the like, do not alter peak widths during separation.

To determine the total analyte concentration or amount, the area or peak height corresponding to each analyte or the amount of each analyte is normalized, e.g., time corrected, and summed. Because the sample aliquot injected into the separation channel is a representative or true sample aliquot, the summation provides a total analyte concentration. In other words, the sample aliquot comprises both fast and slow moving analytes because the injection into the separation channel is appropriately timed to contain all components of the sample. The total analyte amount or concentration is optionally used to determine a ratio of one or more particular analyte to the total.

Measurement Channels

A "measurement channel" or "loading channel," as used herein, refers to a channel or channel region that is used to obtain a measurement on a sample, e.g., by detecting the sample or a portion of the sample within the channel. For example, a sample is flowed through a measurement channel and detected, e.g., by fluorescence. The fluorescent signal obtained is then optionally analyzed, e.g., to determine sample concentration and/or identity.

Figure 3:
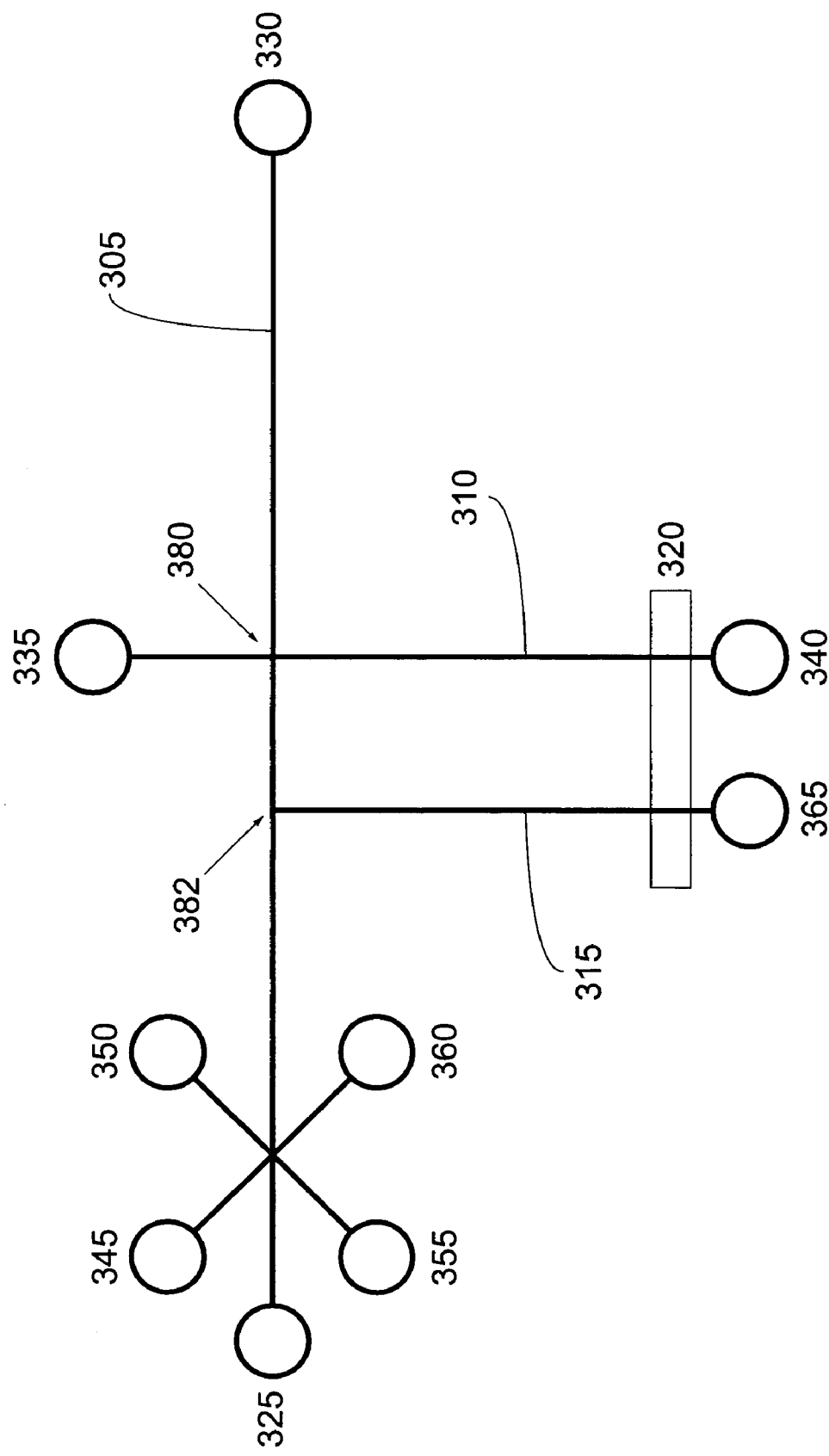
FIG. 3: Schematic illustration of a microfluidic channel configuration comprising a measurement channel for determination of total analyte concentration.

FIG. 3 provides a schematic illustration of a microfluidic device with a measurement channel. A sample is typically flowed, e.g., continuously for a period of time, through a first channel, e.g., channel 305, from a reservoir, e.g., reservoir 325, 345, 350, 355, 360, or the like. At intersection 382, the sample stream is typically split and a first portion flows into measurement channel 315 and a second portion continues to flow through channel 305. The portion in measurement channel 315 is detected in detection region 320. The second portion of the sample flows through intersection 380, at which point, the volume of sample at intersection 380 is cross-injected into separation channel 310. The measurement channel is optionally a separate channel or a portion of a channel, e.g., a portion of channel 305. The measurement channel is optionally downstream or upstream of the separation channel and a device may contain multiple measurement channels. Measurement channels optionally serve as pre-load channels to test multiple samples. One sample is optionally separated in separation channel 310 while another sample is preloaded into measurement channel 315. For example, a first sample is optionally loaded or flowed from reservoir 345 into first channel 305, and into measurement channel 315, where the total analyte concentration is determined. The first sample is also flowed into separation channel 310 for separation and detection of each component. While the first sample is being separated, a second sample is optionally loaded into measurement channel 315, e.g., from reservoir 350. During this load or pre-load, the total analyte concentration is determined and then the second sample is also separated in channel 310 and so forth. The multiple reservoirs are optionally replaced by a sipper capillary that is fluidly coupled during operation to, e.g., a microwell plate comprising a plurality of samples that are sequentially loaded and analyzed. Multiple separation channels and measurement channels are optionally combined into one device to increase sample throughput even more. For example, using the measurement channel to determine the total analyte concentration typically allows the separation to be performed without waiting the specified time and therefore allows a higher throughput.

Once the analytes are flowed into a measurement channel or region, the analytes are detected. When flowed into a measurement channel, the analytes are typically unseparated analytes. As the sample, e.g., mixture of analytes, flows past a detection region proximal to, or within, the measurement channel, the analytes are detected. When electrokinetic flow control is used, the analytes will flow towards the detection region with electrokinetic bias as discussed above. A signal from the analytes, e.g., an absorbance signal, a fluorescence or chemiluminescence signal, a signal due to intercalating dyes, is detected, e.g., continuously, as the sample is flowed through the detection region. As the faster analytes approach the detection region, a signal is observed. The sample is typically continuously flowed toward the detection region and as more and more analytes reach the detection region, the signal height or area increases, e.g., the analyte signal value increases as more of the slower analytes begin to reach the detection region. The value of the signal peak area or height reaches a constant or unchanging value when all of the analytes have reached the detection region. The constant signal value represents the total analyte amount. The faster analytes are still present in the sample when the slow analytes reach the detection region because the sample is typically flowed continuously, i.e., flowed for a period of time and then another sample is flowed for a period of time, and so forth. Therefore, the fast analytes are still flowing through the channel when the slowest analytes reach the intersection. Therefore when the peak height or peak area reaches a constant or steady state value, that value corresponds to the total analyte concentration or amount, which is determined from area under the curve as described above.

The sample is also optionally flowed towards the separation channel, simultaneously or sequentially, to separate a sample aliquot into its various components. The components are detected and their concentrations determined as described above. The individual analyte concentrations are optionally used to determine one or more ratio or difference of individual analyte to total analyte concentration or amount. In addition, the signals from each individual analyte may be summed as described above to provide a duplicate measurement of the total analyte concentration if a representative sample aliquot was used. The two types of measurements are thus used alone or in combination to provide analyte separation and total analyte quantitation. Alternatively, total analyte quantitation techniques are performed without separation of the analytes.

III. Systems for Determining Total Analyte Concentration.

In the present invention, mixtures of analytes are separated and detected and total analyte concentrations are determined. For example, a mixture of nucleic acids is optionally separated into its various components which are each quantitated based on the area of the detected signals. In addition, the total amount or concentration of all the nucleic acids in a sample is determined by methods described herein. Depending on the detected signal measurements, decisions are optionally made regarding subsequent fluidic operations, e.g., whether to assay a particular component in detail to determine, e.g., kinetic information.

The systems described herein generally include microfluidic devices in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Devices

The microfluidic devices of the present invention are used to obtain measurements of total analyte concentration, e.g., in combination with analyte separation. For example, a mixture of analytes is separated, e.g., electrokinetically, into its individual analytes in a separation channel and the total amount of analyte in the mixture is determined, e.g., from a summation of individual analyte peaks or from a total analyte signal. The present devices are configured to provide separation channels and measurement channels to obtain total analyte quantitation and separation of analyte peaks.

The devices generally comprise a body structure with microscale channels fabricated therein. For example, a system of the present invention typically comprises, e.g., an introduction channel and a separation channel. The sizes of the channels are optionally configured to provide good resolution for separations performed in the separation channel. See, e.g., U.S. Ser. No. 60/161,710, by Jaffe et al., entitled "Pressure Induced Reagent Introduction and Electrophoretic Separation," describing the integrated use of shallow channels for electrokinetic separations and deep channels for pressure based manipulations, such as sample introduction and/or mixing. The introduction and separation channels are fluidly coupled to each other and to various reservoirs or other sources of materials. For example, the two channels typically meet or cross to provide an intersection. Alternatively, the introduction channel is a split channel such that the intersection is formed by three channel regions, the two parts of the introduction channel and the separation channel. "Intersection," as used herein, refers to any type of fluid connection between two or more channels. Typical channel intersections are illustrated by intersection 180 in FIG. 1 and intersection region 280 in FIG. 2. Materials are typically electrokinetically loaded and injected from an introduction channel into a separation channel. For example, a cross-injection from an introduction channel into a separation channel injects the volume of fluid at the intersection of the introduction channel and the separation channel into the separation channel. Cross-injections are typically floating injections or pinched injections as described in Ramsey, WO96/04547. For example, in a floating cross-injection, the voltages across the introduction or loading channel are turned off or allowed to float and a voltage is applied across the separation channel. This allows the fluid at the intersection to flow into the separation channel and allows some portion of fluid from the introduction channel to flow into the separation channel as well. In a pinched injection, the voltages across the introduction or loading channel are adjusted to minimize or eliminate leakage, while a voltage is applied across the separation channel thus injecting a plug of fluid from the intersection into the separation channel.

Optionally, the separation channel is a gel filled channel, e.g., a linear polyacrylamide gel filled channel or a polymer solution filled channel, e.g., a polyacrylamide polymer solution or a polydimethylacrylamide/co-acrylic acid polymer, that separates the various components based on molecular weight, wherein each component is eluted from the separation channel with a different retention time. The components are then optionally detected and their molecular weights determined, e.g., by the retention time. In addition, the concentrations and/or amounts of each component are optionally determined based on peak area, peak height, or the like.

A measurement channel is also optionally included in the microfluidic devices and systems in the present invention. A measurement channel typically intersects an introduction channel, but is optionally a region of the introduction channel. The position of the measurement channel is optionally downstream or upstream from the intersection of the separation channel and the introduction channel and multiple measurement channels can be used, e.g., to measure the total analyte concentration, as described above, in multiple samples simultaneously. FIG. 3 illustrates a typical measurement channel, e.g., measurement channel 315. The use of measurement channels is described above.

Detection regions are also included in the present devices. The detection region is optionally a subunit of a channel, such as detection region 120 in FIG. 1. Alternatively, the detection region optionally comprises a distinct channel that is fluidly coupled to the plurality of channels in the microfluidic device. The detection region is optionally located anywhere along the length of the separation channel or region. For example, a detection region located at the most downstream point or end of a separation channel detects the separated components as they exit the separation channel. Detection regions are also typically included in the measurement channels of the invention, for detection of unseparated analytes to determine a total analyte concentration. In some embodiments, a single detector is used that is positioned proximal to both a separation channel and a measurement region, e.g., proximal to detection regions located within each channel.

The detection window or region at which a signal is monitored typically includes a transparent cover allowing visual or optical observation and detection of the assay results, e.g., observation of a colorimetric or fluorometric signal or label. Examples of suitable detectors are well known to those of skill in the art and are discussed in more detail below.

Reservoirs, e.g., for storing, discarding, or supplying, samples, analytes, reagents, buffers, and the like, are also optionally included in the devices of the present invention. For example, a reservoir for a sample or a sample well is optionally located at one end of an introduction channel for introduction of the sample into the introduction channel. The reservoirs are the locations or wells at which samples, components, reagents, and the like are added into the device for assays and/or separations to take place. Introduction of these elements into the system is carried out as described below.

Pressure sources are also optionally applied at the reservoirs of the invention. Typically, channels, such as channel 105 in FIG. 1, connect the reservoirs to a pump or other pressure source(s). For example a vacuum source may be fluidly coupled to the device at a waste reservoir located at the end of a channel, e.g., reservoir 130 at the downstream end of channel 105 in FIG. 1. The vacuum source draws fluid into the channel, e.g., for mixing or reacting with other reagents. Additionally, the vacuum optionally draws any excess or unused material, e.g., material not injected into the separation channel, into a waste reservoir to which the vacuum source is fluidly coupled. Alternatively, a positive pressure source is fluidly coupled to a sample well or reservoir at one end of a channel. The pressure then forces the material into and through the channel. Pressures on the separation channels are optionally adjusted, e.g., individually, to avoid flowing a sample from a separation channel into the waste well.

Electrokinetic forces, e.g., high or low voltages or currents, are also optionally applied at reservoirs to the materials in the channels. For example, voltage gradients applied across a separation channel are used to move fluid down the channel, thus separating the components of the material as they move through the channel at different rates.

Various channel configuration embodiments of the present systems are described above and shown in FIGS. 1, 2, and 3. The channel configurations given above are examples of possible configurations. However, various configurations and dimensions are possible to accommodate the methods described herein. In fact, a variety of microscale systems are optionally adapted to the present invention by incorporating varied channels depths, lengths, separation gels, particle sets, and the like. These devices are described in various PCT applications and issued U.S. patents by the inventors and their coworkers, including U.S. Pat. Nos. 5,699,157 (J. Wallace Parce) issued Dec. 16, 1997, 5,779,868 (J. Wallace Parce et al.) issued Jul. 14, 1998, 5,800,690 (Calvin Y. H. Chow et al.) issued Sep. 1, 1998, 5,842,787 (Anne R. Kopf-Sill et al.) issued Dec. 1, 1998, 5,852,495 (J. Wallace Parce) issued Dec. 22, 1998, 5,869,004 (J. Wallace Parce et al.) issued Feb. 9, 1999, 5,876,675 (Colin B. Kennedy) issued Mar. 2, 1999, 5,880,071 (J. Wallace Parce et al.) issued Mar. 9, 1999, 5,882,465 (Richard J. McReynolds) issued Mar. 16, 1999, 5,885,470 (J. Wallace Parce et al.) issued Mar. 23, 1999, 5,942,443 (J. Wallace Parce et al.) issued Aug. 24, 1999, 5,948,227 (Robert S. Dubrow) issued Sep. 7, 1999, 5,955,028 (Calvin Y. H. Chow) issued Sep. 21, 1999, 5,957,579 (Anne R. Kopf-Sill et al.) issued Sep. 28, 1999, 5,958,203 (J. Wallace Parce et al.) issued Sep. 28, 1999, 5,958,694 (Theo T. Nikiforov) issued Sep. 28, 1999, 5,959,291 (Morten J. Jensen) issued Sep. 28, 1999, 5,964,995 (Theo T. Nikiforov et al.) issued Oct. 12, 1999, 5,965,001 (Calvin Y. H. Chow et al.) issued Oct. 12, 1999, 5,965,410 (Calvin Y. H. Chow et al.) issued Oct. 12, 1999, 5,972,187 (J. Wallace Parce et al.) issued Oct. 26, 1999, 5,976,336 (Robert S. Dubrow et al.) issued Nov. 2, 1999, 5,989,402 (Calvin Y. H. Chow et al.) issued Nov. 23, 1999, 6,001,231 (Anne R. Kopf-Sill) issued Dec. 14, 1999, 6,011,252 (Morten J. Jensen) issued Jan. 4, 2000, 6,012,902 (J. Wallace Parce) issued Jan. 11, 2000, 6,042,709 (J. Wallace Parce et al.) issued Mar. 28, 2000, 6,042,710 (Robert S. Dubrow) issued Mar. 28, 2000, 6,046,056 (J. Wallace Parce et al.) issued Apr. 4, 2000, 6,048,498 (Colin B. Kennedy) issued Apr. 11, 2000, 6,068,752 (Robert S. Dubrow et al.) issued May 30, 2000, 6,071,478 (Calvin Y. H. Chow) issued Jun. 6, 2000, 6,074,725 (Colin B. Kennedy) issued Jun. 13, 2000, 6,080,295 (J. Wallace Parce et al.) issued Jun. 27, 2000, 6,086,740 (Colin B. Kennedy) issued Jul. 11, 2000, 6,086,825 (Steven A. Sundberg et al.) issued Jul. 11, 2000, 6,090,251 (Steven A. Sundberg et al.) issued Jul. 18, 2000, 6,100,541 (Robert Nagle et al.) issued Aug. 8, 2000, 6,107,044 (Theo T. Nikiforov) issued Aug. 22, 2000, 6,123,798 (Khushroo Gandhi et al.) issued Sep. 26, 2000, 6,129,826 (Theo T. Nikiforov et al.) issued Oct. 10, 2000, 6,132,685 (Joseph E. Kersco et al.) issued Oct. 17, 2000, 6,148,508 (Jeffrey A. Wolk) issued Nov. 21, 2000, 6,149,787 (Andrea W. Chow et al.) issued Nov. 21, 2000, 6,149,870 (J. Wallace Parce et al.) issued Nov. 21, 2000, 6,150,119 (Anne R. Kopf-Sill et al.) issued Nov. 21, 2000, 6,150,180 (J. Wallace Parce et al.) issued Nov. 21, 2000, 6,153,073 (Robert S. Dubrow et al.) issued Nov. 28, 2000, 6,156,181 (J. Wallace Parce et al.) issued Dec. 5, 2000, 6,167,910 (Calvin Y. H. Chow) issued Jan. 2, 2001, 6,171,067 (J. Wallace Parce) issued Jan. 9, 2001, 6,171,850 (Robert Nagle et al.) issued Jan. 9, 2001, 6,172,353 (Morten J. Jensen) issued Jan. 9, 2001, 6,174,675 (Calvin Y. H. Chow et al.) issued Jan. 16, 2001, 6,182,733 (Richard J. McReynolds) issued Feb. 6, 2001, and 6,186,660 (Anne R. Kopf-Sill et al.) issued Feb. 13, 2001; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, WO 99/44217, WO 99/56954, WO 99/64836, WO 99/64840, WO 99/64848, WO 99/67639, WO 00/07026, WO 00/09753, WO 00/10015, WO 00/21666, WO 00/22424, WO 00/26657, WO 00/42212, WO 00/43766, WO 00/45172, WO 00/46594, WO 00/50172, WO 00/50642, WO 00/58719, WO 00/060108, WO 00/070080, WO 00/070353, WO 00/072016, WO 00/73799, WO 00/078454, WO 00/102850, and WO 00/114865.

For example, pioneering technology providing cell based microscale assays are set forth in U.S. Pat. No. 5,942,443, by Parce et al. "High Throughput Screening Assay Systems in Microscale Fluidic Devices" and, e.g., in 60/128,643 filed Apr. 4, 1999, entitled "Manipulation of Microparticles In Microfluidic Systems," by Mehta et al. Complete integrated systems with fluid handling, signal detection, sample storage and sample accessing are available. For example, U.S. Pat. No. 5,942,443 provides pioneering technology for the integration of microfluidics and sample selection and manipulation.

The devices described above are used in the present invention, e.g., to separate a mixture of analytes, to determine total analyte concentration or amount, to determine concentration or amount of individual analytes, and the like.

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquotting, and the like. Similarly, downstream operations may include similar operations, including, e.g., labeling of components, assays and detection operations, electrokinetic or pressure-based injection of components into contact with particle sets, or materials released from particle sets, or the like.

Fluid Direction System and Fluid Control Elements

A variety of controlling instrumentation is optionally utilized in conjunction with the microfluidic devices described above, for controlling the transport and direction of fluidic materials and/or materials within the devices of the present invention, e.g., by pressure-based or electrokinetic control. In general, analytes and/or other components or reagents are flowed in a microscale system by electrokinetic (including either electroosmotic or electrophoretic) techniques, or by using pressure-based flow mechanisms, or combinations thereof. In the present system, electrokinetic transport is typically used. For example, various analytes are transported through the first channel or introduction channel by electrokinetic gradients, which causes electrokinetic bias in the sample aliquot injected into the separation channel unless an appropriate time passes, e.g., to allow the slowest analytes to reach the cross-injection intersection. After the appropriate time, a representative sample aliquot is obtained and a total analyte concentration is optionally determined.

In the present system, the fluid direction system controls the transport, flow and/or movement of a sample through the microfluidic device. For example, the fluid direction system optionally directs the pressure-based movement of a sample into the device, e.g., through a sipper capillary. The fluid direction system also directs electrokinetic based movement of samples, e.g., into and through a separation channel. Electrokinetic based movement though the separation channel results in separated analytes. In particular, the fluid direction system directs movement of at least two analytes through the first channel region; movement of the at least two analytes from the first channel region into the measurement channel region; movement of the at least two analytes through the first detection region; movement of the at least two analytes from the first channel into the separation channel, thereby producing two or more separated analytes; and/or, movement of the two or more separated analytes through the second detection region.

Electrokinetic material transport systems or electrokinetic controllers are used in the present invention to provide movement of analytes, reagents, and the like, through microfluidic channels. "Electrokinetic material transport systems," as used herein, include systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of nucleic acids, proteins, enzymes, cells, modulators, etc. suspended within the fluid. Similarly, the components, e.g., polynucleotides, polypeptides, proteins, antibodies, carbohydrates, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis. For example, nucleic acids which have similar charge/mass ratios are optionally separated based on size in a channel comprising a size-discriminant separation matrix, such as polyacrylamide.

Typically, the electrokinetic material transport and direction systems of the invention rely upon the electrophoretic mobility of charged species within the electric field applied to the structure. Such systems are more particularly referred to as electrophoretic material transport systems. For example, in the present system, separation of a mixture of components into its individual components optionally occurs by electrophoretic separation. For electrophoretic applications, the walls of interior channels of the electrokinetic transport system are optionally charged or uncharged. Typical electrokinetic transport systems are made of glass, charged polymers, or uncharged polymers. The interior channels are optionally coated with a material that alters the surface charge of the channel.

A variety of electrokinetic controllers and systems which are optionally used in the present invention are described, e.g., in Ramsey WO 96/04547, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 by Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., regularly pulsed field(s) causing the sample to oscillate direction of travel) flow of labeled components in one or more channels toward a waste reservoir. Particularly, modulation of the voltages applied at the various reservoirs, such as reservoirs 325, 330, 340, 365, and the like in FIG. 3, can move and direct fluid flow through the interconnected channel structure of the device.

Other methods of transport are also available for situations in which electrokinetic methods are not desirable. For example, sample introduction and reaction are optionally carried out in a pressure-based system and high throughput systems typically use pressure induced sample introduction. In addition, cells are desirably flowed using pressure-based flow mechanisms.

Pressure based flow is also desirable in systems in which electrokinetic transport is also used. For example, pressure based flow is optionally used for introducing and reacting reagents in a system in which the products are electrophoretically separated. Therefore, in the present invention, pressure-based systems are optionally combined with the electrokinetic transport systems described above.

Pressure can be applied to microscale elements to achieve fluid movement using any of a variety of techniques. Fluid flow (and flow of materials suspended or solubilized within the fluid, including cells or other particles) is optionally regulated by pressure based mechanisms such as those based upon fluid displacement, e.g., using a piston, pressure diaphragm, vacuum pump, probe, or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces. For example, pressure is optionally generated via compression of air, in which case air, not liquid, is used as the coupling medium.

Internal sources of fluid transport include microfabricated pumps, e.g., diaphragm pumps, thermal pumps, lamb wave pumps, and the like that have been described in the art. See, e.g., U.S. Pat. Nos. 5,271,724, 5,277,556, and 5,375,979 and Published PCT Application Nos. WO 94/05414 and WO 97/02357. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467, filed Jan. 28, 1999.

In some embodiments, a vacuum source is applied to a reservoir or well at one end of a channel to draw the suspension through the channel. For example, a vacuum source is optionally placed at a reservoir in the present devices for drawing fluid into a channel, e.g., a vacuum source at reservoir 330 in FIG. 3 applies a pressure to channel 305, thus drawing fluid from reservoir 325, 345, 350, 355, 360, or the like into channel 305.

Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Another alternative to electrokinetic transport is an electroosmotic pump which uses electroosmotic forces to generate pressure based flow. See, e.g., published International Application No. WO 99/16162 by Parce, entitled "Micropump." An electroosmotic pump typically comprises two channels. The pump utilizes electroosmotic pumping of fluid in one channel or region to generate pressure based fluid flow in a connected channel, where the connected channel has substantially no electroosmotic flow generated Hydrostatic, wicking and capillary forces are also optionally used to provide pressure for fluid flow of materials such as enzymes, substrates, modulators, or protein mixtures. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al, U.S. Ser. No. 09/245,627, filed Feb. 5, 1999. In these methods, an adsorbent material or a branched capillary structure is placed in fluidic contact with a region where pressure is applied, thereby causing fluid to move towards the adsorbent material or branched capillary structure. The capillary forces are optionally used in conjunction with the electrokinetic or pressure-based flow in the present invention to draw fluid through the channels, e.g., the measurement channel. The capillary action pulls material through a channel. For example a wick is optionally added to a channel to aid fluid flow by drawing liquid through the channel.

Mechanisms for reducing adsorption of materials during fluid-based flow are described in U.S. Ser. No. 09/310,027, "PREVENTION OF SURFACE ADSORPTION IN MICROCHANNELS BY APPLICATION OF ELECTRIC CURRENT DURING PRESSURE-INDUCED FLOW" filed May 11, 1999 by Parce et al. In brief, adsorption of cells, components, proteins, nucleic acids, and other materials to channel walls or other microscale components during pressure-based flow can be reduced by applying an electric field such as an alternating current to the material during flow. Such an electric current can cause electrokinetic biasing of the analytes as they flow through the channel. For example, in the present invention pressure based flow is optionally used in combination with an alternating current to provide fluid flow through the introduction channel or first channel, the measurement channel, or the like. The introduction of electrokinetic bias to the samples is compensated for by the methods provided herein.

In an alternate embodiment, microfluidic systems can be incorporated into centrifuge rotor devices, which are spun in a centrifuge. Fluids and particles travel through the device due to gravitational and centripetal/centrifugal pressure forces.

Typically, the fluid control elements described above are controlled and/or coordinated by controller systems appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

The above transport and control systems are optionally used in the systems of the present invention, alone or in combinations, to provide fluid flow through the channels of the invention. In addition to transport through the microfluidic system, the invention also provides for introduction of sample or reagents, e.g., enzymes, proteins, substrates, modulators, and the like, into the microfluidic system.

Sources of Assay Components and Integration with Microfluidic Formats

Reservoirs or wells are provided in the present invention as sources of samples, mixtures of analytes, analytes, reagents, buffers, and the like, or as waste wells. Such wells include, e.g., reservoirs 225, 230, 235, and 240 in FIG. 2. For example, a sample is optionally introduced into the device through reservoir 225.

Sources of samples, e.g., mixtures of analytes such as polynucleotides, polypeptides, and the like, are fluidly coupled to the microchannels noted herein in any of a variety of ways. In particular, those systems comprising sources of materials set forth in Knapp et al. "Closed Loop Biochemical Analyzers" (WO 98/45481; PCT/US98/06723) and Parce et al. "High Throughput Screening Assay Systems in Microscale Fluidic Devices" WO 98/00231 and, e.g., in 60/128,643 filed Apr. 4, 1999, entitled "Manipulation of Microparticles In Microfluidic Systems," by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others.

For example, the source of a sample, mixture of components, or buffer can be a microwell plate external to the body structure, having, e.g., at least one well with the selected cell type or component. Alternatively, samples are contained in a well disposed on the surface of the body structure, a reservoir disposed within the body structure; a container external to the body structure comprising at least one compartment comprising the samples, or a solid phase structure comprising the samples or reagents in lyophilized or otherwise dried form. For example, in FIG. 3, various wells are comprised within the device. Reservoirs 325, 345, 350, 355, and 360 each typically comprise a different sample. Additional reservoirs are optionally included.

A loading channel region is optionally fluidly coupled to a pipettor channel with a port external to the body structure. The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like.

The integrated microfluidic system of the invention optionally includes a very wide variety of storage elements for storing samples and reagents to be assessed. These include well plates, matrices, membranes and the like. The reagents are stored in liquids (e.g., in a well on a microtiter plate), or in lyophilized form (e.g., dried on a membrane or in a porous matrix), and can be transported to an array component, region, or channel of the microfluidic device using conventional robotics, or using an electropipettor or pressure pipettor channel fluidly coupled to a region or channel of the microfluidic system.

Detectors

Once separated, the components of a sample are typically detected. In the present invention, the entire sample, e.g., an unseparated sample, is also optionally detected, e.g., before separation. For example, a mixture of polynucleotides is optionally detected to determine a total analyte concentration, e.g., in a measurement channel, and separated and detected in a separation channel. In another embodiment, the sample is separated using a representative sample aliquot, and the detected signals from the separated components are summed to determine total analyte concentration. The detector(s) optionally monitors one or a plurality of signals, e.g., from one or more analyte of interest, in a separation channel or in the measurement channel. For example, the detector optionally monitors an optical signal, e.g., an analyte signal, that corresponds to a labeled analyte, such as a labeled nucleic acid or polypeptide, located in a detection region or detection channel, e.g., a detection region that is proximal to or within a separation channel. In another embodiment, the detector is positioned at the downstream end of the separation region or channel and detects a plurality of signals from the separated components as they elute from a separation matrix.

Nucleic acids, proteins, polynucleotides, polypeptides, antibodies, or other components which can emit a detectable signal, e.g., fluorescein labeled analytes, are optionally flowed past the detector, or, alternatively, the detector can move relative to the array to examine various positions in the array (or, the detector can simultaneously monitor a number of spatial positions corresponding to channel regions, e.g., as in a CCD array). In other embodiments, the analytes are unlabeled analytes, e.g., unlabeled nucleic acids or polynucleotides, that are detected using an intercalating dye, e.g., a fluorescent dye that inserts into a nucleic acid double helix.

The detector typically includes or is operably linked to a computer, e.g., which has software for converting detector signal information into assay result information, e.g., molecular weight based on retention time or elution time, identity of a analyte, concentration of an analyte, total analyte concentration, or the like.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "proximal," to a particular element or region, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. For example fluorescent or chemiluminescent detectors are typically preferred. In some embodiments, absorbance is used to detect, e.g. nucleic acids. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the material's spectral characteristics. In preferred aspects, the detector measures an amount of light emitted from the material, such as a fluorescent or chemiluminescent material. As such, the detection system will typically include collection optics for gathering a light based signal transmitted through the detection window and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as fluorescently labeled intercalating dues used to detect nucleic acids, the detector typically includes a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources are required for other detection systems. For example, broad band light sources, e.g., in conjunction with appropriate optical filters to select wavelength(s) of interest, are typically used in light scattering/transmissivity detection schemes, and the like. Typically, light selection parameters are well known to those of skill in the art.

The detector can exist as a separate unit, but is preferably integrated with a controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the fluid direction system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. For example, the software optionally directs the fluid direction system to transport the sample into a first channel of the device or into a separation channel, e.g., using electrokinetic forces. In addition, the software optionally directs the fluid direction system to inject or cross inject a sample aliquot from the first channel into the separation channel in which the analytes are separated. Any other movement necessary to assay, separate, or detect the sample is also optionally directed by the software instructions.

The computer additionally receives the data from the one or more sensors/detectors included within the system, and interprets the data, and either provides it in a user understood format, or uses that data to initiate further controller instructions in accordance with the programming, e.g., such as in monitoring and control of flow rates, temperatures, applied voltages, and the like.

In the present invention, the computer typically includes software for the monitoring of materials in the channels. Additionally the software is optionally used to control electrokinetic or pressure-modulated injection or withdrawal of material.

In addition, the computer optionally includes software for deconvolution of the signal or signals from the detection system. Computer software instruction sets are typically used in the present invention to determine the total analyte concentration, each individual analyte concentration, one or more ratios of analyte concentration to total analyte concentration, or the like, based on analyte and total analyte peak areas (area under the curve), heights, and/or amplitudes which correspond to the amount of analyte detected (for example, deconvolution quantitates the amount of each analyte in a sample, the total amount of analyte present in a sample and calculates ratios between the two. The analyte amounts, e.g., of individual analytes or total analyte, are calculated, e.g., based on peak area which corresponds to the amount of material detected). The peak areas are determined, e.g., by integration of the area under the curve produced by a signal plot. The concentration is determined by correlating the amount of material detected based on peak area to the amount of fluid flowed through the detection region during detection. For example when a representative sample aliquot of a known volume (the volume is optionally determined as it flows past the detector, e.g., into a waste reservoir) is injected into a separation channel and the separated analytes detected. The signal peaks corresponding to the separated analytes are integrated, e.g., using computer software for integration, to determine the amount of material detected. The total amount of material is determined by summing the signal peak areas and the concentration is determined by dividing the amount of material by the volume of the sample aliquot detected.

Kits

Generally, the microfluidic devices described herein are optionally packaged to include reagents for performing the device's preferred function. For example, the kits can include any of the microfluidic devices described along with assay components, reagents, sample materials, particle sets, salts, separation matrices, control/calibrating materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (e.g., enzymatic inhibitors, microbicides/bacteriostats, anticoagulants), the physical stabilization of the material, e.g., through immobilization on a solid support, entrapment in a matrix (e.g., a gel), lyophilization, or the like.

Kits also optionally include packaging materials or containers for holding a microfluidic device, system or reagent elements.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated herein by reference in their entirety for all purposes to the same extent as if each individual publication or patent document were specifically and individually indicated to be incorporated by reference.

What is claimed is:

1. A method for separating analytes and determining a total analyte concentration or amount, the method comprising:
    (i) electrokinetically flowing at least two analytes through a first channel;
    (ii) waiting a specified time, during which specified time the at least two analytes flow into an intersection of the first channel and a separation channel;
    (iii) injecting the at least two analytes at the intersection into the separation channel;
    (iv) separating the at least two analytes in the separation channel, which separating results in two or more separated analytes;
    (v) detecting the two or more separated analytes, which detecting results in two or more individual analyte signals; and,
    (vi) determining a total analyte concentration or amount from the two or more individual analyte signals, wherein each of the two or more signals comprises an area or peak height, and wherein the determining step comprises summing the areas of the two or more signals or summing the peak heights of the two or more signals to determine the total analyte concentration or amount.

2. The method of claim 1, wherein the at least two analytes are known analytes for which flow rates at specified voltages are known, and wherein the specified time is determined based on the known flow rates.

3. The method of claim 1, wherein the at least two analytes have different electrokinetic mobilities, wherein at least one of the at least two analytes comprises a slowest analyte, and waiting the specified time comprises waiting until the slowest analyte reaches the intersection.

4. The method of claim 1, wherein the separating step comprises electrophoretically separating the at least two analytes.

5. The method of claim 1, wherein the method further comprises determining a concentration or amount of at least one of the two or more separated analytes based on the individual analyte signal of the at least one separated analyte.

6. The method of claim 5, the method further comprising calculating a ratio or difference of the amount of at least one of the at least two analytes to the total analyte amount or to a portion of the total analyte amount.

* * * * *